(12) United States Patent
Weltmann et al.

(10) Patent No.: US 10,307,606 B2
(45) Date of Patent: Jun. 4, 2019

(54) DEVICE FOR GENERATING PLASMA, SYSTEM FOR GENERATING PLASMA AND METHOD FOR GENERATING PLASMA

(71) Applicant: Leibniz-Institut für Plasmaforschung und Technologie e.V., Greifswald (DE)

(72) Inventors: Klaus-Dieter Weltmann, Binz (DE); Ronny Brandenburg, Groß Kiesow (DE); Manfred Stieber, Greifswald (DE); Stefan Horn, Loissin (DE); Philipp Turski, Greifswald (DE)

(73) Assignee: Leibniz-Institut für Plasmaforschung und Technologie e.V., Greifswald (DE)

( * ) Notice: Subject to any disclaimer, the term of this patent is extended or adjusted under 35 U.S.C. 154(b) by 0 days.

(21) Appl. No.: 15/352,630

(22) Filed: Nov. 16, 2016

(65) Prior Publication Data
US 2017/0136252 A1    May 18, 2017

(30) Foreign Application Priority Data
Nov. 17, 2015    (EP) .................................... 15195015

(51) Int. Cl.
*H05H 1/24* (2006.01)
*A61N 1/44* (2006.01)
(Continued)

(52) U.S. Cl.
CPC .............. *A61N 1/44* (2013.01); *A61B 18/042* (2013.01); *A61L 2/14* (2013.01); *H05H 1/2406* (2013.01);
(Continued)

(58) Field of Classification Search
CPC .................. A61N 1/44; H05H 1/2406; H05H 2001/2437; H05H 2001/2412; H05H 2001/2431; A61B 18/042; A61L 2/14
(Continued)

(56) References Cited

U.S. PATENT DOCUMENTS 3,263,137 A  *  7/1966  Muller ..................... H01G 9/04
                                               361/436
2006/0133970 A1 *  6/2006  Imanishi ................ B01D 53/92
                                               422/186
(Continued)

FOREIGN PATENT DOCUMENTS

DE      202009011521        12/2010
DE      102013203648         9/2014
(Continued)

*Primary Examiner* — Douglas W Owens
*Assistant Examiner* — Amy X Yang
(74) *Attorney, Agent, or Firm* — Soroker Agmon Nordman

(57) ABSTRACT

A device for generating plasma (1) comprises a high voltage electrode (10) as well as at least one external electrode (11, 12), wherein the high voltage electrode (10) at least in one coordinate direction (34) is arranged between conductive material of at least one external electrode (11, 12). The high voltage electrode (10) is covered with a dielectric (21) at least one side facing an external electrode (11, 12). Between the respective external electrode (11, 12) and the high voltage electrode (10) over its longitudinal extension at least one spacer element (20) is present, which at least in the region of its arrangement electrically insulates the respective external electrode (11,12) from the high voltage electrode (10) and which positions the respective external electrode (11, 12) at a constant distance from the high voltage electrode (10), wherein the spacer element is a gas-permeable foil.

11 Claims, 4 Drawing Sheets

(51) Int. Cl.
*A61B 18/04* (2006.01)
*A61L 2/14* (2006.01)

(52) U.S. Cl.
CPC ............ *H05H 2001/2412* (2013.01); *H05H 2001/2431* (2013.01); *H05H 2001/2437* (2013.01)

(58) Field of Classification Search
USPC .............. 315/111.21, 111.31, 111.81, 111.41
See application file for complete search history.

(56) References Cited

U.S. PATENT DOCUMENTS

| | | | |
|---|---|---|---|
| 2012/0271225 A1* | 10/2012 | Stieber | A61B 18/042 604/26 |
| 2014/0182879 A1 | 7/2014 | Busse | |
| 2015/0088234 A1* | 3/2015 | Weltmann | A61B 18/042 607/104 |
| 2016/0008500 A1* | 1/2016 | Ehlbeck | A61L 2/14 427/230 |

FOREIGN PATENT DOCUMENTS

| | | | | |
|---|---|---|---|---|
| WO | 2010138102 | | 12/2010 | |
| WO | WO 2010138102 A1 * | | 12/2010 | ........... A61B 18/042 |
| WO | 2011023478 | | 3/2011 | |
| WO | 2013167693 | | 11/2013 | |

* cited by examiner

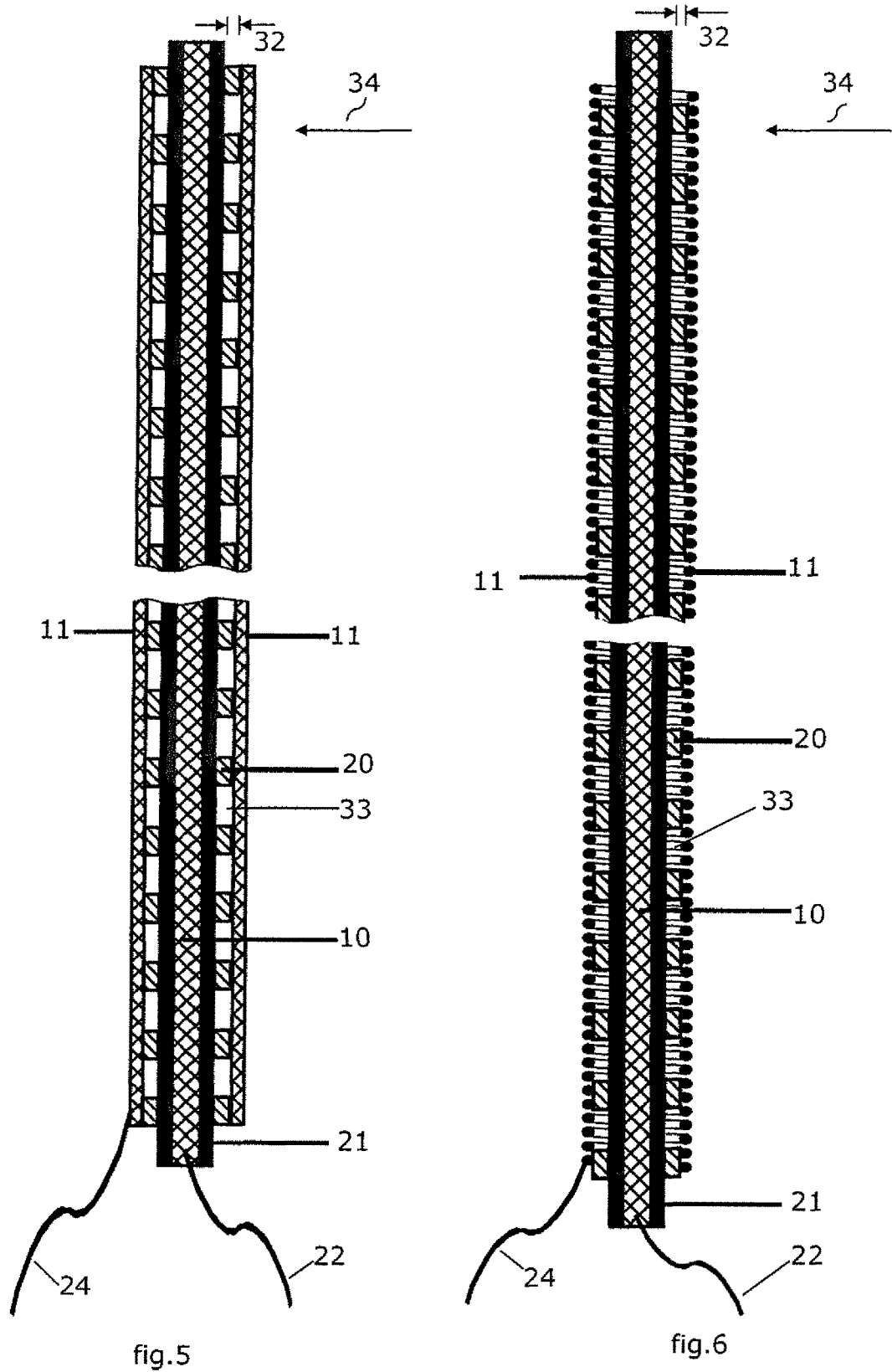

DEVICE FOR GENERATING PLASMA, SYSTEM FOR GENERATING PLASMA AND METHOD FOR GENERATING PLASMA

The present application relates to a device for generating plasma with a high voltage electrode as well as at least one external electrode. Furthermore, the present invention relates to a system for generating plasma with several inventive devices for generating plasma, as well as a method for generating plasma by means of an inventive device for generating plasma or an inventive system for generating plasma.

The device for generating plasma serves the purpose of planar, antimicrobial treatment of moist surfaces and thus offers a possibility of antimicrobial wound treatment in a moist environment by means of atmospheric pressure plasma sources.

Atmospheric pressure plasma sources can be used for medical, dental or cosmetic purposes. Conventional devices for generating plasma provide for a superposition of jet plasmas for the coverage of an area. In the process, various jet nozzle geometries are used.

Along with pointwise application, attempts are made to also use plasmas in planar manner, for example for the treatment of wounds. With such planar design devices, ordinarily a dielectric barrier discharge (DBD) is implemented. In the process one differentiates between two different electrode configurations: an arrangement for generating surface dielectric barrier discharge (SBD), in which the electrodes are arranged on both sides of a dielectric directly on the surface of the dielectric and the plasma is formed on the surface of the dielectric, and an arrangement for generating a volume dielectric barrier discharge (VBD), in which the two electrodes (at least one with a dielectric) are arranged at a short distance from one another and the plasma forms in this space between the two electrodes.

Such devices are usually made from a relatively solid or rigid raw material for reasons of material strength. Therefore, an adaptation to specified topographies is only possible to a limited extent.

In particular devices for generating plasma, which are designed for application in the medical field, are subject to relatively strict regulations regarding safety from a risk of injury from the high voltage connection as well as with respect to the compliance with the guidelines of electromagnetic compatibility (EMC).

A planar device for generating plasma is for example known from WO 2011/023478 A1. This anticipated device is a collar for treatment of human or animal skin with the help of a cold atmospheric pressure plasma. The collar consists of a high voltage electrode, an insulating elastomer, a dielectric and a grounded electrode. The planar high voltage electrode is for one thing limited by a planar, insulating elastomer and for another by a planar dielectric. On the opposite side of the dielectric there is a planar, grounded electrode. In the case of the application of a high voltage this arrangement leads to surface dielectric barrier discharge. For use of the collar on the afflicted skin of the human body the high voltage electrode, the insulating elastomer, the dielectric and the electrode are flexible and can be placed on any curved surface.

A further device for generating plasma is disclosed in WO 2013/167693 A1. This also discloses a device for treatment of areas of human or animal surfaces by means of a cold atmospheric pressure plasma by generating surface barrier discharge. This device for generating plasma of WO 2013/167693 A1 consists of a wire-shaped high voltage electrode with an applied grounded electrode. For the surface dielectric discharge the high voltage electrode is sheathed with a dielectric which forms a flexible unit. The grounded electrode consists of a conducting, textile material. Thus, the device for generating plasma adapts to the contour of the body areas to be treated.

The use of the above-mentioned device for generating plasmas is disadvantageous for wound treatment of biological tissue in moist environments. The devices of WO 2011/023478 A1 as well as WO 2013/167693 A1 are based on the generation of surface dielectric barrier discharge. This type of generation is significantly impaired or even completely suppressed by the high humidity on the surface of the dielectric.

The impairment due to high humidity can be counteracted using a volume dielectric barrier discharge device. A plasma generation device based on a volume dielectric barrier discharge is disclosed in WO 2011/076193 A1. The device of WO 2011/076193 A1 consists of a planar high voltage electrode, which is limited on the front and on the rear by a planar dielectric. This electrode arrangement can be flexibly adapted to the contour of the surface. The surface of the front dielectric is characterized by studs at an equidistant height. In conjunction with a grounded, electrically conducting surface in the air conductance areas between the studs a dielectrically impeded volume dielectric barrier discharge is generated.

However, the use of the surface to be treated as a grounded counter electrode has the disadvantage of uncontrollable or undefinable surface effects on the biological tissue to be treated. Further the studs serving as spacers lie directly on the wound to be treated and cause undesirable irritations or grid-shaped decontaminations.

The devices known from the prior art for generating plasma with planar atmospheric pressure plasma sources have disadvantages for medicinal use. A use of atmospheric pressure plasma sources for medicinal, dental or cosmetic purposes is only possible when compliance with the guidelines of electromagnetic compatibility (EMC) can be guaranteed. In the case of the above mentioned planar plasma sources, the interference radiation through the plasma source itself can no longer be neglected, the essential EMC requirements are not met.

The present invention addresses the problem of providing a device for generating plasma, a system for generating plasma as well as a method for generating plasma, with which in manner that is simple, cost-effective, harmless from the standpoint of safety as well as being able to be applied flexibly a treatment of surfaces, in particular a disinfection or sterilization of surfaces such as e.g. also biological tissue, is possible.

This problem is solved by the inventive device for generating plasma according to claim 1 as well as by the inventive system for generating plasma according to a system claim and by the inventive method for generating plasma according to a method claim. Advantageous embodiments of the inventive device for generating plasma are specified in the the dependent claims.

The inventive device for generating plasma in particular serves the purpose of generation of an atmospheric pressure plasma for the antimicrobial treatment of damp surfaces. The device for generating plasma comprises a high voltage electrode as well as at least one external electrode, wherein the high voltage electrode is arranged at least in a coordinate direction between conductive material of at least one external electrode. The high voltage electrode is covered at least on one side facing an external electrode with a dielectric. If necessary, the high voltage electrode is completely covered with a dielectric. Between the respective external electrode and the high voltage electrode at least one spacer element is arranged over its longitudinal extension, which at least in the region of its arrangement electrically insulates the respective external electrode from the high voltage electrode and positions it at a constant distance, wherein the spacer element is a gas-permeable foil.

The conductive material of the external electrode opposite the high voltage electrode in at least one coordinate direction serves the purpose in the event of the application of a suitable electrical voltage to the device for generating plasma as the actual external electrode.

Preferably the dielectric is not only present at the side of the high voltage electrode facing the respective external electrode, but rather encloses the high voltage electrode thus provided.

Through the spacer element or through the arrangement of several spacer elements an essentially equidistant arrangement of the electrodes to one another is realized. As a result, the possibility of generating a volume barrier discharge arises, which is significantly more stable vis-a-vis a severely wet environment, so that the inventive device for generating plasma can in particular be used advantageously on wounds or biological tissues. Furthermore, through the external electrode or external electrodes arranged on both sides of the high voltage electrode a significant reduction of the electromagnetic interference radiation radiated from the plasma source is achieved.

The high voltage electrode must be configured for the high voltage (HV) range, namely for a voltage of at least 1 kV. In one embodiment of the inventive device for generating plasma the dielectric of the high voltage electrode is designed for double the electric strength (thus at least 2 kV). In the process the device for generating plasma can be equipped for a voltage range of 1 kV to 25 kV, in the case of a frequency of the AC voltage of 1 kHz Kilohertz to 1 Mhz, wherein the activation can take place with sine, square or rectangular wave as well as also pulsed.

The external electrode or external electrodes are grounded. In one embodiment of the inventive device for generating plasma it comprises a first external electrode and a second external electrode, wherein the high voltage electrode also referred to as internal electrode is arranged between the two external electrodes.

In this case the high voltage electrode on the sides facing the two external electrodes is covered with a dielectric.

The high voltage electrode can be implemented as a conducting element, whose proportion of the length to the diameter is at least 10. Such a thin conducting element can be a thin insulated wire or also an insulated electrically conductive thread.

The high voltage electrode can be configured as an insulated wire, wherein the insulation in the process simultaneously embodies the dielectric.

In one embodiment of the device for generating plasma the high voltage electrode has a form of a meander or spiral-shaped course.

In one further design alternative, the high voltage electrode and/or the external electrode or external electrodes can be configured as electrically conductive textile material in the form of a mesh, weave, knitted fabric or knit or also a stitch-bonded fabric, non-woven fabric or felt or a combination of these textile materials, wherein the material used is metal or also only a metal coating and in the case of the high voltage electrode this material is coated with a dielectric.

In one further embodiment, the external electrode is configured as an electrically conductive foil. In the process the foil is in particular perforated and/or structured.

In addition, or as an alternative the high voltage electrode can also be designed as a foil coated with a dielectric.

The respective material embodying the high voltage electrode as well as also the external electrode or external electrodes as well as if applicable also the dielectric, insulation and the spacer element can have an elasticity module of a maximum of $1 \times 10^9$ N/m$^2$, in particular an elasticity module between $0.1 \times 10^9$ N/m$^2$ and $0.5 \times 10^9$ N/m$^2$, so that also the entire device has this elasticity module and thus a very slight bending and/or torsional stiffness. The use of elastic or flexible materials enables the flexible adaptation of the device for generating plasma to a wide range of topographies.

In one embodiment, the whole device for generating plasma has a a total elasticity of $0.1 \times 10^9$ N/m$^2$ to $1 \times 10^9$ N/m$^2$, so that the whole device for generating plasma is adaptable to any threedimensional shape of surfaces.

The external electrode is configured in one embodiment of the device for generating plasma as a gas-permeable and flexible electrode including the high voltage electrode, such as e.g. as a metal fabric or also another electrically conductive, textile material or a perforated, electrically conductive elastomer foil an elastomer foil coated with an electrically conductive material, such as e.g. a silicone foil.

In one embodiment, the whole device for generating plasma is gas-permeable as well as liquid-permeable.

The external electrode is grounded and can also be a tube made of a perforated or woven conductive material or of spiral arranged thin stainless steel. The external electrodes used in the inventive device for generating plasma are conductively connected to one another.

In one further embodiment of the inventive device for generating plasma provision is made that the device for generating plasma has several spacer elements, which are designed as insulation pieces enclosing the high voltage electrode at least in sections. Such spacer elements, also referred to as distance pieces can be e.g. silicone tube pieces. In one embodiment provision is made that a spacer element or also several spacer elements enclose the high voltage electrode over its entire course.

In one further embodiment of the device for generating plasma provision is made that the spacer element is planar in design. That means that the spacer element extends essentially in a straight plane, so that it separates the external electrodes, preferably likewise extending in straight, planar levels as well as the high voltage electrode in between.

The spacer element can in this embodiment be realized by a perforated, preferably spatially inclusive and comprehensive gas-permeable foil made of an electrically non-conductive elastomer. Such foil, such as e.g. a silicone foil, can also be used as a dielectric, wherein a wire-shaped high voltage electrode, which e.g. is also present as a mesh, weave, fabric or knitted fabric, is embedded in this foil.

In one embodiment, the spacer element is a foil or gauze made of an electrically non-conductive material.

Such a foil can have openings, so that the foil serving as dielectric is gas-permeable. The openings can be produced by perforation.

In particular, the foil should have this embodiment when the foil is designed to be spatially inclusive and comprehensive between the electrodes.

In a further embodiment variant of the device for generating plasma provision is made that the spacer element is configured as a mesh, weave, fabric or knitted fabric. As a result, openings are integrated in the spacer element. As an alternative, provision can be made that punctiform or grid-shaped coatings are produced on such a spacer element, in order to be able to observe the required distance between the electrodes for a dielectrically impeded volume discharge.

In supplementary embodiment, the inventive device for generating plasma comprises a power supply unit which is configured to apply a low to high frequency high voltage between the external electrode or the external electrodes and the high voltage electrode.

Advantageous embodiments of the device for generating plasma with respect to the material of the electrodes as well as also with respect to the power supply unit, the supply lines and connections of the leads to the electrodes are taught in documents WO2011023478A1 as well as WO2013167693A1, whose disclosures in this regard are included in their entirety in the present patent application.

Thus, one general embodiment of the inventive device for generating plasma consists in the fact that the device for generating plasma is essentially planar, wherein a planar high voltage electrode is enclosed in sandwich-like fashion by two planar external electrodes.

One further embodiment consists in a bar-shaped or tubular design, wherein a longitudinally extended high voltage electrode is enclosed by a spiral or screw-thread shaped external electrode. One further alternative lies in the fact that an oblong high voltage electrode is enclosed by a tubular external electrode made of a gas-permeable, electrically conductive material. If flexible material is used in the case of these embodiments, they can be in spiral or meander shaped planar arrangement, so that also in these cases an adaptation to specified topographies is possible.

All embodiments have in common the fact that spacer elements are arranged between the high voltage electrode and the material of the external electrode, so that in each case a distance exists between the high voltage electrode and external electrode for the realization of a volume barrier discharge.

As a result, an effective, antimicrobial plasma treatment of wounds and biological tissues is made possible, even in a very damp environment. Due to the external electrode or external electrodes arranged on both sides of the high voltage electrode a significant reduction of the electromagnetic interference radiation radiated from the plasma source is achieved. This makes it possible to meet the conditions for compliance with the guidelines of electromagnetic compatibility (EMC) also for planar plasma sources, so that an inventive plasma device can also be approved for use for medicinal, dental and cosmetic purposes.

In contrast to plasma sources, that are based on surface barrier discharge, in which case the formation of a plasma on the surface of the dielectric is significantly impeded or even suppressed through high humidity, the present device for generating plasma is, due to the volume dielectric barrier discharge, significantly more suitable for dampness and thus also suitable for the effective, antimicrobial plasma treatment of wounds and biological tissues in very damp environments.

In contrast to plasma sources, which, while carrying out the dielectrically impeded volume discharge, use the surface of the biological tissue to be treated as a grounded counter or external electrode and thus jeopardize the tissue through uncontrolled or undefined surface effects (such as e.g. in the case of an electrical breakdown of the insulation of the high voltage electrode), the inventive device for generating plasma ensures the elimination of this danger through the provided arrangement of at least one external electrode on both sides of the high voltage electrode.

For optimum wound compatibility, the inventive device for generating plasma can comprise a gas-permeable wound dressing, which in the wound treatment is to be positioned between the biological tissue and the device for generating plasma. Such a wound dressing can be a thin, relatively broad-meshed textile wound dressing (e.g. sterile gauze). This prevents the plasma source from coming directly into contact with the wound and prevents undesirable irritations or also a contamination of the wound as in the case of the direct application of non-sterile devices for generating plasma.

Another aspect of the present invention is a system for generating plasma, which is in particular suitable for large-scale treatment of surfaces, such as e.g. burns. This system for generating plasma comprises several inventive devices for generating plasma as well as one or more power supply units, which can be or are electrically connected to the devices for generating plasma. In particular, the devices for generating plasma of the system for generating plasma can be in matrix-like arrangement or also linear arrangement, in order to be able to cover correspondingly shaped or dimensioned surface areas. Thus, several inventive devices for generating plasma can be merged to one greater plasma source, in order e.g. to be able to treat larger skin areas of burn victims rapidly, flexibly as well as in a medically harmless manner. In the process, for the power supply there is the possibility of using a single high-performance voltage source as well as also several identical voltage sources for supplying a single area element and thus also for supplying power to a respective voltage generating device.

The present invention is supplemented by a method for generating plasma, in particular for generating a volume dielectric barrier discharge, in which an inventive device for generating plasma or also an inventive system for generating plasma is provided and an electrical high voltage is applied to the high voltage electrode and at least one external electrode. As a result of this, in particular a disinfection of surfaces, such as e.g. wounds of human or animal tissue, can be performed, in which the method for generating plasma is carried out at such a distance to the surface to be disinfected that the surface to be disinfected comes into contact with the reactive species of the plasma gas generated by the plasma.

Further details and advantages of the present invention arise from the following description of exemplary embodiments in conjunction with the drawing.

FIGS. 1 and 2 show a planar device for generating plasma in round shape, wherein FIG. 1 shows the device for generating plasma in exploded view and FIG. 2 shows the device for generating plasma in assembled representation.

FIGS. 3 and 4 show a planar device for generating plasma in square shape, wherein FIG. 3 shows the device for generating plasma in exploded view and FIG. 4 shows the device for generating plasma in assembled representation.

FIGS. 5 and 6 show a schematic of a linear device for generating plasma, wherein FIG. 5 shows the device for generating plasma with a tubular external electrode and FIG. 6 shows the device for generating plasma with a spiral-shaped external electrode.

Figure 1:
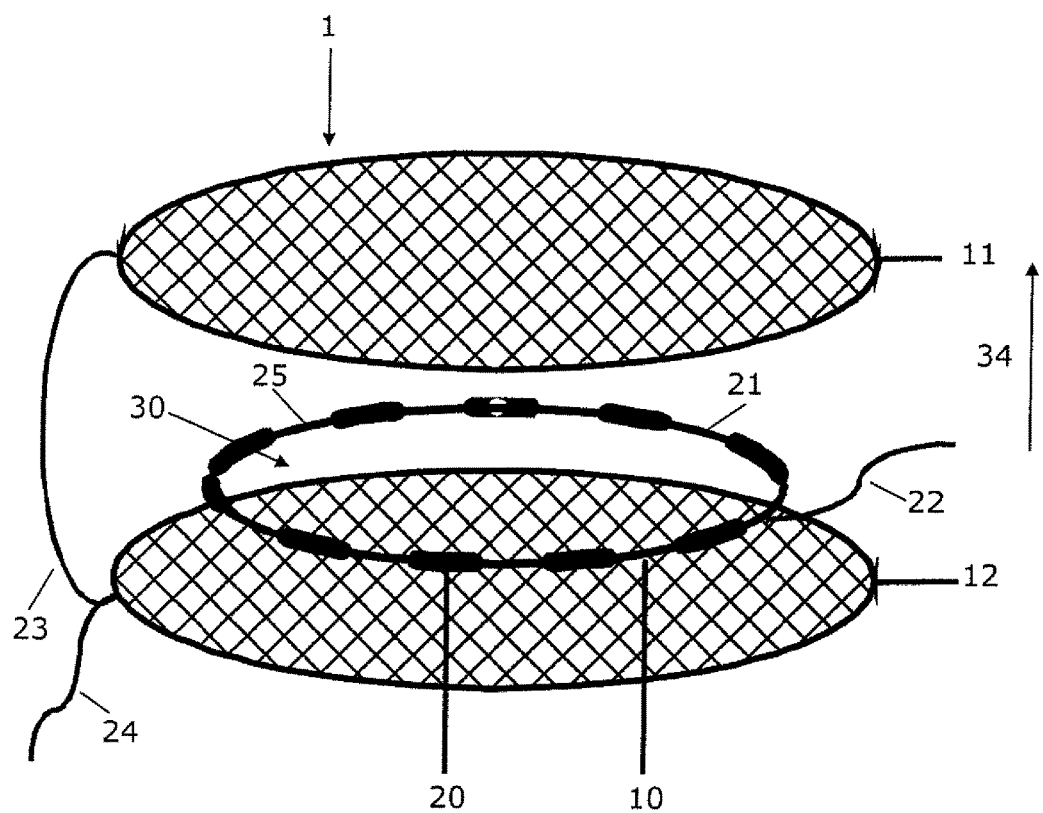

FIG. 1 shows a first exemplary embodiment of a device for generating plasma 1 in exploded view. The device for generating plasma 1 comprises a high voltage electrode 10 enclosing an area 30. In both directions of the normals of this enclosed area 30 there is an external electrode 11, 12. The two external electrodes 11, 12 are connected to one another via an electrical connection 23. The high voltage electrode 10 is configured as wire in this example and is fed through the connection cable 22. The two external electrodes 11, 12 are configured in this example as metal fabric and grounded via the ground cable 24. For a volume dielectric barrier discharge the high voltage electrode 10 is sheathed with a dielectric 21. In order to ensure the necessary equidistant distance 32 for the volume dielectric barrier discharge between the high voltage electrode 10 covered with a dielectric 21 and the grounded external electrode 11, the high voltage electrode 10 is equipped with spacer elements 20, so-called spacers. Here, the spacer elements 20 are suitable silicone tube pieces, which however are only present at sections of the high voltage electrode 10 over its longitudinal extension, so that free sections 25 remain in between, in which the plasma is generated.

Figure 2:
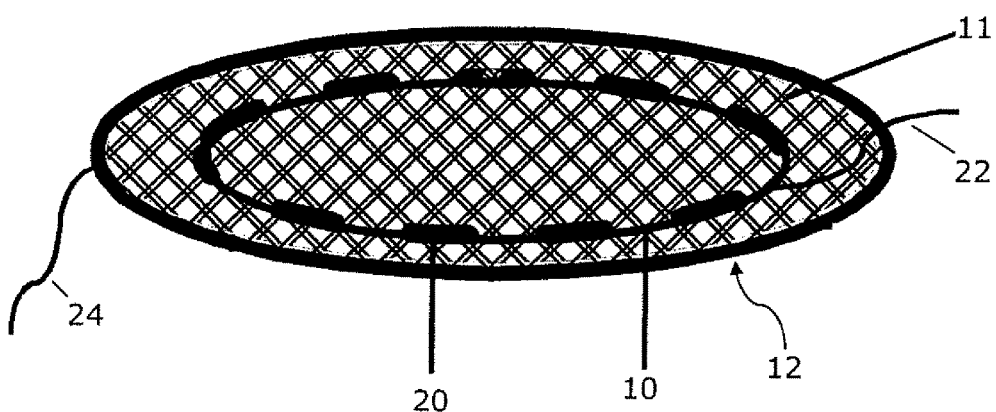

In the applicable state the device for generating plasma 1 is configured according to the representation in FIG. 2. In this connection, the spacer elements 20 define the distance between the grounded external electrodes 11, 12 and the high voltage electrode 10. The device for generating plasma 1 represented in 2 has two sides, which are configured by the two external electrodes 11, 12. Both sides are applicable for placement on a wound of a human tissue to be treated, wherein for better compatibility the device for generating plasma 1 with can be combined with a thin, gas-permeable wound dressing not shown here.

Figure 3:
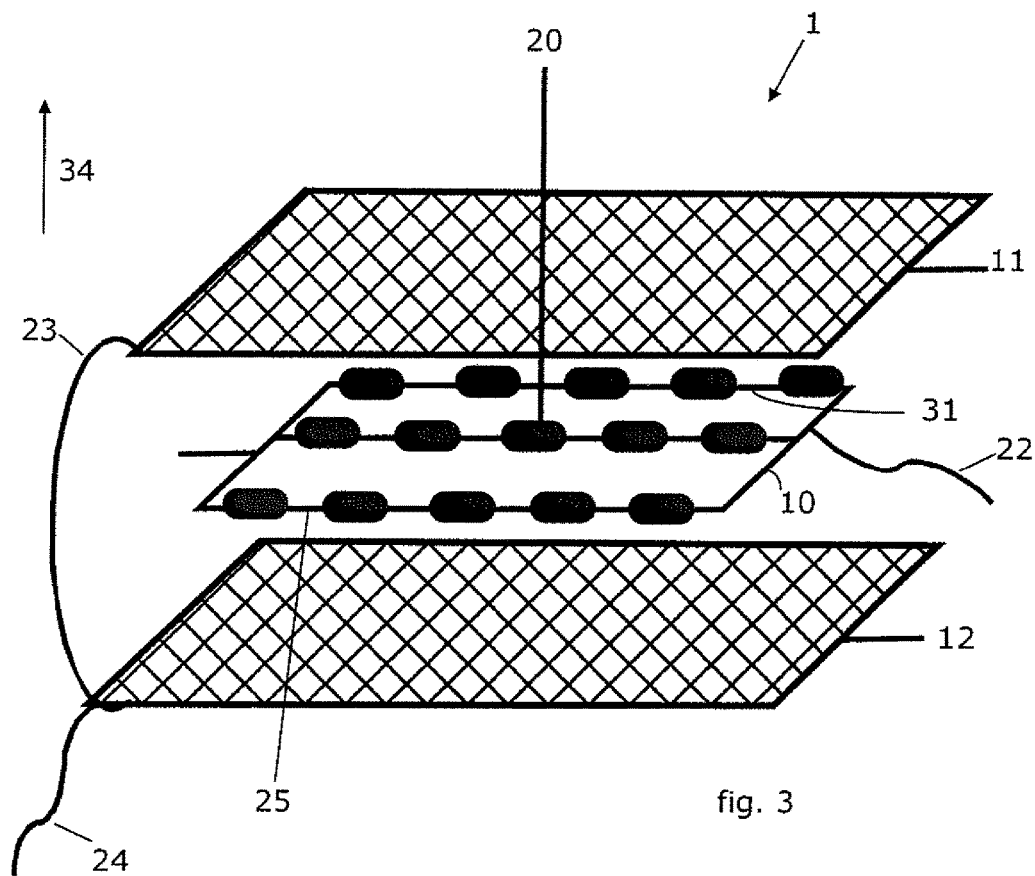

FIG. 3 shows a further embodiment in exploded view. As shown in the exemplary embodiment represented in FIGS. 1 and 2, here the planar high voltage electrode 10 is limited in each case by a planar external electrode 11, 12 in in both directions of the normals of the area 30 enclosed by the high voltage electrode 10. Furthermore, also in this exemplary embodiment the external electrodes 11, 12 implemented by a metal fabric. Both external electrodes 11, 12 are connected to one another through the electrical connection 23 and grounded via the ground cable 24.

In contrast to the exemplary embodiment represented in FIGS. 1 and 2 here the device for generating plasma 1 is implemented in a rectangular shape. That means the metal fabric of the two external electrodes 11, 12 has a rectangular design. The high voltage electrode 10 with the connection cable 22 has, in contrast to the exemplary embodiment represented in FIGS. 1 and 2, parallel sections 31, so that also the high voltage electrode 10 forms a rectangular shape. The necessary distance 32 for the dielectrically impeded volume discharge is also ensured here through spacer elements 20. The spacer elements 20 are suitable silicone tube pieces.

Figure 4:
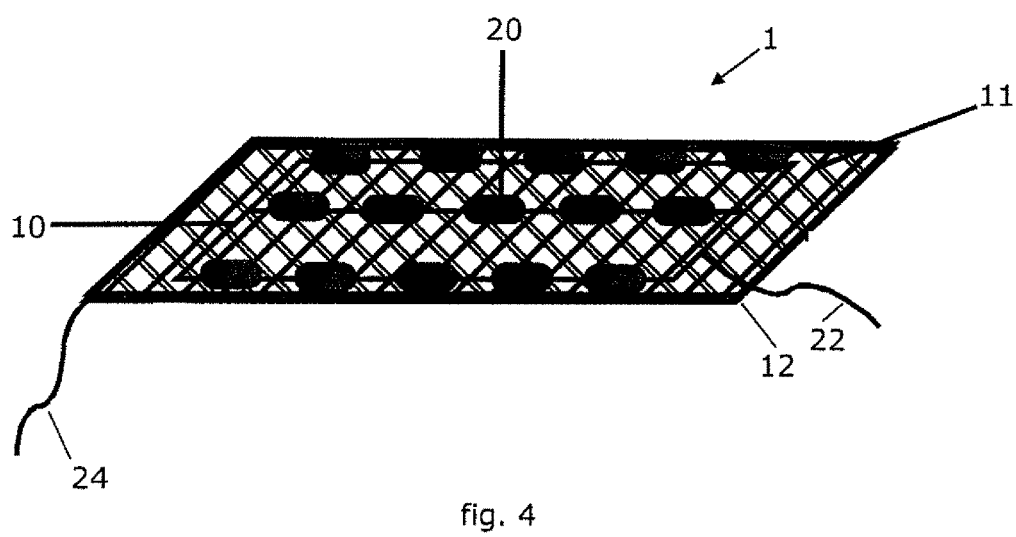

FIG. 4 shows the exemplary embodiment of the device for generating plasma 1 in the applicable shape.

The sectional view in FIG. 5 shows an example of a linear design of an inventive device for generating plasma. In FIG. 5 the wire-shaped high voltage electrode 10 is sheathed with a dielectric 21. The tubular external electrode 11 encloses the high voltage electrode 10 and is grounded via the ground cable 24. The necessary equidistant distance 32 for the dielectrically impeded volume discharge is given by the spacer elements 20. The atmospheric pressure plasma 33 generated for the dielectrically impeded volume discharge is located in the volume between the spacer elements 20, the grounded external electrode 11 and the dielectric 21. From the represented coordinate direction 34 it is obvious that the high voltage electrode 10 is arranged at least in the coordinate direction 34 between conductive material of the external electrode 11.

A further design of the linear device for generating plasma 1 is represented in FIG. 6. The linear high voltage electrode 10, which is sheathed with a dielectric 21, is enclosed by a spiral-shaped external electrode 11. This spiral-shaped external electrode 11 is grounded via the ground cable 24. Here too the equidistant distance 32 between the high voltage electrode 10 and the external electrode 11, which is necessary for the dielectrically impeded volume discharge, is to be maintained by spacer elements 20. The atmospheric pressure plasma 33 is generated in the spaces limited by the external electrode 11, the high voltage electrode 10 and the individual spacer elements 20.

Figure 7:
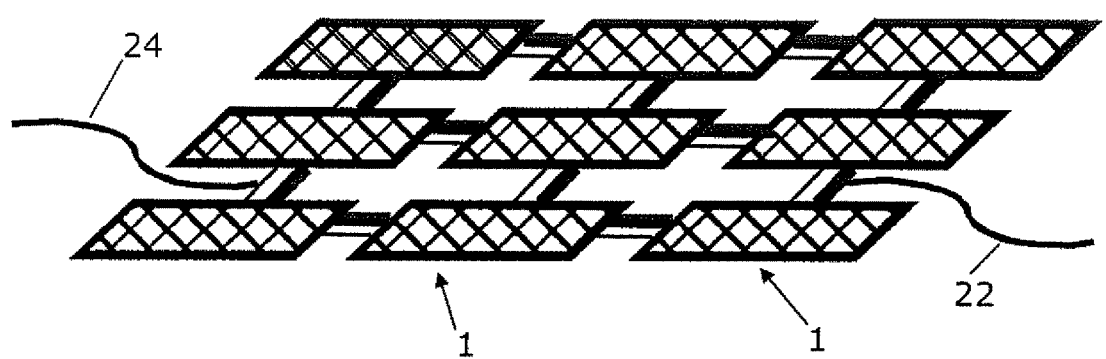
FIG. 7 shows a system for generating plasma with several devices for generating plasma in rectangular design.

The aforementioned exemplary embodiments relate to the design of an individual device for generating plasma 1. In FIG. 7 is a system for generating plasma can be seen, which has several devices for generating plasma, in particular for the large-scale treatment of surfaces.

In this system for generating plasma several devices for generating plasma 1 are in square shape in cascade connection with one another. The connection shown between the individual devices for generating plasma 1 for one thing lead to the high voltage, which is connected with the connection cable 22, and for another to a grounded connection, which is connected with the ground cable 24.

REFERENCE LIST

Device for generating plasma 1
High voltage electrode 10
First external electrode 11
Second external electrode 12
Spacer element 20
Dielectric 21
Connection cable 22
Electrical connection 23
Ground cable 24
Free section 25
Enclosed area 30
Parallel section 31
Distance 32
Atmospheric pressure plasma 33
Coordinate direction 34

The invention claimed is:

1. A device for generating plasma (1), comprising; a high voltage electrode (10) in the form of a wire sheathed with a dielectric at least one extremal electrode (11, 12), wherein the at least one external electrode (11, 12) is grounded; one or more spacer elements (20) in the form of silicone tube pieces of a gas-permeable foil positioned over sections of a longitudinal extension of the high voltage electrode (10), wherein the spacer elements (20) position the at least one external electrode (11, 12) at a constant distance from the high voltage electrode (10); wherein the high voltage electrode (10) is arranged at least in a coordinate direction (34) between or adjacent to conductive material of the at least one external electrode (11, 12); wherein the device for generating plasma (1) comprises a first external electrode (11) and a second external electrode (12), wherein the high voltage electrode (10) is arranged between the first external electrode (11) and the second external electrode (12).

2. The device for generating plasma according to claim 1, characterized in that the high voltage electrode (10) has a form of a meander or spiral-shaped course.

3. The device for generating plasma according to claim 1, characterized in that the high voltage electrode (10) is present as a mesh, weave, fabric or knitted fabric.

4. The device for generating plasma according to claim 1, characterized in that the at least one external electrode (11, 12) is present as a mesh, weave, fabric or knitted fabric.

5. The device for generating plasma according to claim 1, characterized in that the at least one external electrode (11 and 12) is configured as an electrically conductive foil, in particular as perforated and/or structured foil.

6. The device for generating plasma according to claim 1, characterized in that the spacer element (20) is configured as a mesh, weave, fabric or knitted fabric.

7. The device for generating plasma according to claim 1, characterized in that the device for generating plasma (1) has a power supply unit, which is configured to apply a low to high frequency high voltage between the at least one external electrode (11, 12) and the high voltage electrode (10).

8. A system for generating plasma, comprising several devices for generating plasma (1) according to claim 1 as well as one or more power supply units, which are electrically connected to the devices for generating plasma (1).

9. A method for generating plasma, in which a device for generating plasma according to claim 1, comprising several devices for generating plasma (1) according to claim 1 is provided and an electrical high voltage is applied to the high voltage electrode (10) and the at least one external electrode (11, 12).

10. The device for generating plasma according to claim 1, wherein the high voltage electrode (10) encloses an area (30) for generating plasma; wherein the area (30) is confined by the first external electrode (11) and the second external electrode (12) respectively positioned on opposite sides normal to the area (30).

11. A system for generating plasma, comprising several devices for generating plasma (1) according to claim 1 is provided and an electrical high voltage is applied to the high voltage electrode (10) and the at least one external electrode (11, 12).

* * * * *